United States Patent
Parr et al.

[11] Patent Number: 5,443,512
[45] Date of Patent: Aug. 22, 1995

[54] ORTHOPAEDIC IMPLANT DEVICE

[75] Inventors: Jack E. Parr, North Webster; Roy D. Crowninshield; Thirumalai N. C. Devanathan, both of Warsaw; Helen Chu, Goshen, all of Ind.

[73] Assignee: Zimmer, Inc., Warsaw, Ind.

[21] Appl. No.: 111,234

[22] Filed: Aug. 24, 1993

Related U.S. Application Data

[60] Division of Ser. No. 15,044, Feb. 8, 1993, abandoned, which is a continuation of Ser. No. 605,335, Oct. 30, 1990, abandoned.

[51] Int. Cl.⁶ ............................................. A61F 2/28
[52] U.S. Cl. ................................... 623/16; 623/18; 623/22; 623/23
[58] Field of Search ................... 623/16, 18, 20, 22, 623/23

[56] References Cited

U.S. PATENT DOCUMENTS

| | | | |
|---|---|---|---|
| 3,662,405 | 5/1972 | Bortz et al. | |
| 3,893,196 | 7/1975 | Hochman | |
| 3,905,777 | 9/1975 | Lacroix | |
| 3,938,198 | 2/1976 | Kahn et al. | |
| 3,964,473 | 6/1976 | Wickham et al. | |
| 4,202,055 | 5/1980 | Reiner et al. | |
| 4,205,400 | 6/1980 | Shen et al. | |
| 4,213,816 | 7/1980 | Morris | 156/245 |
| 4,237,559 | 12/1980 | Borom | |
| 4,249,270 | 2/1981 | Bahler et al. | |
| 4,351,069 | 9/1982 | Ballintyn et al. | |
| 4,356,571 | 11/1982 | Esper et al. | |
| 4,406,023 | 9/1983 | Harris | 623/22 |
| 4,454,612 | 6/1984 | McDaniel et al. | |
| 4,479,271 | 10/1984 | Bolesky et al. | |
| 4,535,485 | 8/1985 | Ashman et al. | 623/16 |
| 4,536,894 | 8/1985 | Galante et al. | 623/22 |
| 4,550,448 | 11/1985 | Kenna | 623/16 |
| 4,568,348 | 2/1986 | Johnson et al. | 623/20 |
| 4,589,883 | 5/1986 | Kenna | 623/22 |
| 4,608,052 | 8/1986 | Van Kamper et al. | 623/22 |
| 4,636,214 | 1/1987 | Homsy | 623/16 |
| 4,636,219 | 1/1987 | Pratt et al. | 623/22 |
| 4,650,109 | 3/1987 | Crivella et al. | 623/18 X |
| 4,650,489 | 3/1987 | Thompson | 623/16 |
| 4,662,887 | 5/1987 | Turner et al. | 623/16 |
| 4,673,409 | 6/1987 | Van Kampen | 623/23 |
| 4,714,467 | 12/1987 | Lechner et al. | 623/16 |
| 4,718,912 | 1/1988 | Crowninshield | 623/23 |
| 4,750,905 | 6/1988 | Koeneman et al. | 623/16 |
| 4,778,469 | 10/1988 | Lin et al. | 623/16 |
| 4,828,565 | 5/1989 | Dethoit et al. | 623/22 |
| 4,828,566 | 5/1989 | Griss | 623/18 X |
| 4,851,004 | 7/1989 | Homsy | 623/16 |
| 4,854,496 | 8/1989 | Bugle | 623/22 X |
| 4,889,685 | 12/1989 | Shimamune et al. | 623/16 X |
| 4,919,665 | 4/1990 | Homsy | 623/18 |
| 4,938,772 | 7/1990 | Frey et al. | 623/23 |
| 4,938,774 | 7/1990 | Tepic | 623/23 |
| 4,997,444 | 3/1991 | Farling | 623/16 |
| 5,002,580 | 3/1991 | Noble et al. | 623/23 |
| 5,019,108 | 5/1991 | Bertin et al. | 623/23 |
| 5,047,054 | 9/1991 | Vijayan et al. | 623/16 |
| 5,176,712 | 1/1993 | Homsy | 623/23 |
| 5,201,766 | 4/1993 | Georgette | 623/22 X |
| 5,222,985 | 6/1993 | Homsy | 623/23 |
| 5,236,457 | 8/1993 | Devanathan | 623/18 X |
| 5,290,318 | 3/1994 | Ling et al. | 623/18 X |

FOREIGN PATENT DOCUMENTS

| | | |
|---|---|---|
| 0420435 | 4/1991 | European Pat. Off. |
| 2163960 | 3/1986 | United Kingdom. |
| 2184458 | 6/1987 | United Kingdom. |
| 2216425 | 10/1989 | United Kingdom. |

OTHER PUBLICATIONS

BASF Plastics Ultrapek, B 607e 10.89.

*Primary Examiner*—Mary Beth O. Jones
*Attorney, Agent, or Firm*—Todd A. Dawson

[57] ABSTRACT

An orthopaedic implant device is formed from, or defined by, a combination of different materials. These devices include a body metal component and a porous metal surface layer for intimate contact with bone and a polymer in the form of a casing that includes adhesive characteristics for attachment to the body metal component and the porous metal layer. The preferred polymer casing is polyaryletherketone.

8 Claims, 1 Drawing Sheet

ORTHOPAEDIC IMPLANT DEVICE

This is a division of application Ser. No. 08/015,044, abandoned, filed Feb. 8, 1993, which is a continuation of application number 07/605,335, filed Oct. 30, 1990, now abandoned.

FIELD OF THE INVENTION

The present invention relates to an orthopaedic implant device, such as, a hip or knee joint prosthesis utilized to replicate joint articulation of the skeletal structure following implantation in a patient.

BACKGROUND OF THE INVENTION

In current orthopaedic practice it is known to provide metal orthopaedic implants to repair or reconstruct joint movement for a patient. These metal orthopaedic implants are commonly made from cobalt chrome, titanium and stainless steel. Moreover, with cobalt chrome implants it is possible to provide a porous layer of cobalt chrome beads for intimate contact with bone to accommodate bone ingrowth into the porous layer. In a similar manner, titanium implants are provided with titanium beads or fiber metal pads in the form of a porous layer for bone ingrowth.

In contrast to the metal orthopaedic implants, U.S. Pat. No. 4,750,905, issued to James Koeneman et al on Jun. 14, 1988, teaches a composite hip prosthesis wherein nonmetallic components are assembled with a carbon fiber core, a woven fiber sheath and a thermoplastic resin skin forming the outer contour of a hip prosthesis.

A hybrid metallic/nonmetallic orthopaedic device is taught in U.S. Pat. No. 4,454,612, issued to John McDaniel on Jun. 19, 1984, wherein a metal core is covered with a thin polymer coating and a polymer fiber layer is attached to the coating to accommodate bone ingrowth.

One of the inventors of the present invention has proposed a substantially nonmetallic composite core with a porous metal surface embedded into the outer surface of the core to define a hybrid metallic/nonmetallic orthopaedic implant device. In U.S. Pat. No. 5,219,363 Roy Crowninshield, et al discloses a core made of fibers, a casing made from a polymer such as, polyetheretkerketone and a porous metal surface embedded into the outer surface of the polymer.

The aforegoing prior art addresses the issue of stress transfer in orthopaedic devices so that the interface between the orthopaedic device and the remaining bone does not impart substantially different loads to the remaining bone than ordinarily imparted prior to resection of bone. If the stress applied to the bone is not controlled excessive stresses may fracture the remaining bone stock while on the other hand stress shielding may result in bone resorption.

SUMMARY OF THE INVENTION

The present invention teaches an orthopaedic implant device with a polymer in the form of a casing to adhesively attach a body, or core to a porous metal surface. In addition, the polymer adhesive in the case of a hip prosthesis generates a substantial volume of the hip prosthesis so that the body or core is relatively small in size resulting in a flexible hip prosthesis. By controlling the dimension of the body or core the flexibility of the hip prosthesis is substantially equated with that of the surrounding bone.

In a preferred embodiment of a hip prosthesis, the core is constructed from cobalt chrome and the porous layer is constructed from titanium fiber metal while the polymer adhesive is polyaryletherketone or Ultrapek ® KR4177 polymer as manufactured by BASF. This polymer manifested aggressive adhesive characteristics to the metallic surface of the cobalt chrome and the titanium following transformation to a heated state.

It is an advantage of the present invention that the polymer adhesive not only adhesively couples the porous layer relative to the core but also generates strength characteristics for the resulting orthopaedic implant device.

DETAILED DESCRIPTION

Figure 1:
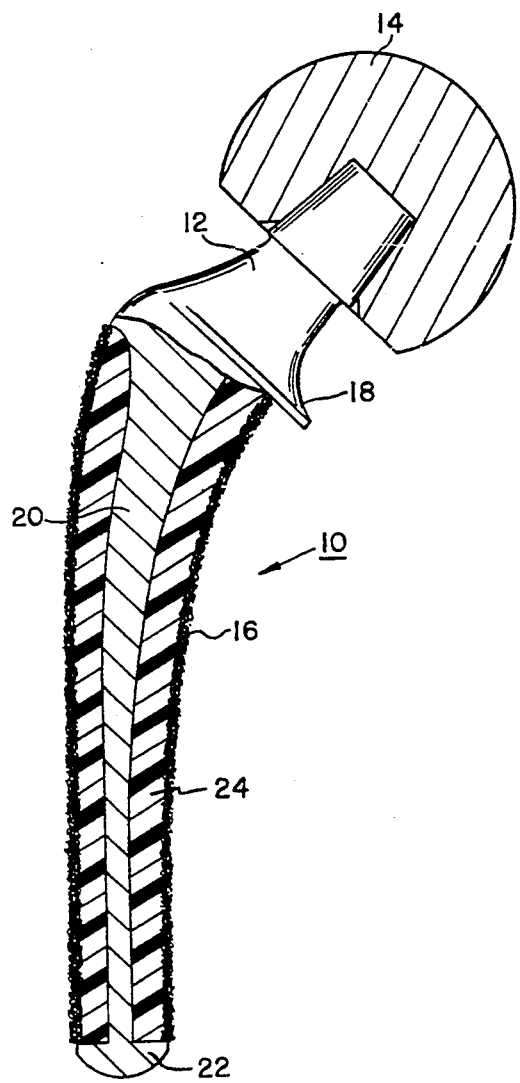
FIG. 1 is a side view of a hip prosthesis that is cut away longitudinally to illustrate the construction therefore.

The orthopaedic implant device in FIG. 1 illustrates a hip prosthesis 10 with a neck 12 at a proximal end adapted to fixedly receive a modular head 14. From the neck 14 to a distal end the hip prosthesis is provided with a porous surface or layer 16 to accommodate bone ingrowth in uncemented surgical procedures. However, the porous layer 16 could also allow for bone cement infiltration if a cemented surgical procedure is followed. The neck 12 includes a collar 18 forming a lower boundary for the collar 18. An internal core or body 20 extends distally from the neck 12 to an integral end cap 22. A polymer casing 24 is adhesively secured to the core 20 and porous layer 16 in a manner to be described hereinafter to securely connect the porous layer 16 with the core 20.

The core 20 and neck 12 are preferably made from cobalt chrome which is sufficiently sized to permit a reduced diameter for the core 20 over most of its length in comparison to the neck 12. The diameter of the core 20 is reduced uniformly in a distal direction up to but not including the end cap 22.

The polymer casing is preferably made of Ultrapek ® KR4177 which is a polyaryletherketone (PAEK) polymer sold by BASF. Ultrapek is a tradename of BASF for a partially crystalline, thermoplastic polycondensation resin. Experiments with this polymer casing indicated that substantial adhesion forces can be obtained when the polymer casing 24 is injection molded to the core 20.

The porous surface layer 16 is made from titanium fiber metal as disclosed in U.S. Pat. 3,906,550 issued to Rostoker and Galante. With titanium fiber metal as the porous layer, it is possible to melt the porous layer partially into the polymer casing 24 so that adhesion and mechanical interlock secure the porous surface layer 16 to the polymer casing 24.

In order to construct the hip prosthesis of FIG. 1, the core 20 is placed within a die of an injection molding machine. The neck 12 and end cap 22 are used to center the core 20 within the die. The polymer is injection molded into the die around the core 20 at a temperature of about 770° F. to form the polymer casing 24. the metal core may also be preheated to a temperature of about 800° F. prior to the injection molding of the polymer. During heating in the injection molding machine, the core 20 is surrounded by nitrogen argon or subjected to vacuum to minimize oxidation of the surface of the core 20 to enhance adhesive bonding between the core 20 and the polymer. The core 20 and polymer casing are removed from the die and cooled to room temperature. Next, the porous surface layer is heated to about 770° F. and pressed into engagement with the polymer casing. The heated porous layer 16 melts the outer surface of the polymer casing 24 to penetrate therein. When a portion of the porous layer 16 is embedded into the polymer casing 24, further penetration is halted so that the polymer casing 24 and the porous surface layer 16 are cooled together. With the temperature reduced, the polymer casing 24 remains adhered to the porous layer 16 which is also embedded into the polymer casing 24. The polymer casing is rigid at room temperature to also physically retain the porous layer connected thereto.

A test of the adhesion characteristics of Ultrapek KR 4177 polymer was designed to compare ultimate tensile strength for cobalt chrome and titanium metals. A pair of cylindrical rod samples with 0.6 square inch faces were adhered together with Ultrapek KR4177 fully engaging the faces. The Ultrapek KR 4177 polymer was melted at about 770° F. in a furnace with the faces engaging the melted polymer for 45 minutes. After heating the samples and polymer were cooled to room temperature. With the pair of samples adhered together by the polymer, a separation force was applied to the samples to measure what force was required to separate the polymer from either sample. For cobalt chrome with clean faces the tensile strength was 17 Ksi which is the ultimate tensile strength of the polymer. The cobalt chrome faces were cleaned, glass bead blasted and passivated before engagement with the polymer.

Similar testing of titanium resulted in a tensile strength of 7 Ksi. However if the titanium samples are titanium nitride coated or surface reacted by means of thermal exposure to nitrogen before the polymer is adhered thereto the tensile strength is increased to 10 Ksi. In addition, if the samples of titanium and polymer are heated by induction for 4 minutes as opposed to a furnace, the tensile strength is increased to 13 Ksi. This latter increase is believed to result from a thinner oxide layer on the titanium surface in the induction heating process as contrasted to a thicker oxide layer formed in the furnace. The oxide layer formed on the titanium surface with induction heating is reduced because of the short time (4 minutes) required to fully adhere the polymer to the sample faces, as contrasted to the 45 minutes required in the furnace heating process.

Figure 2:
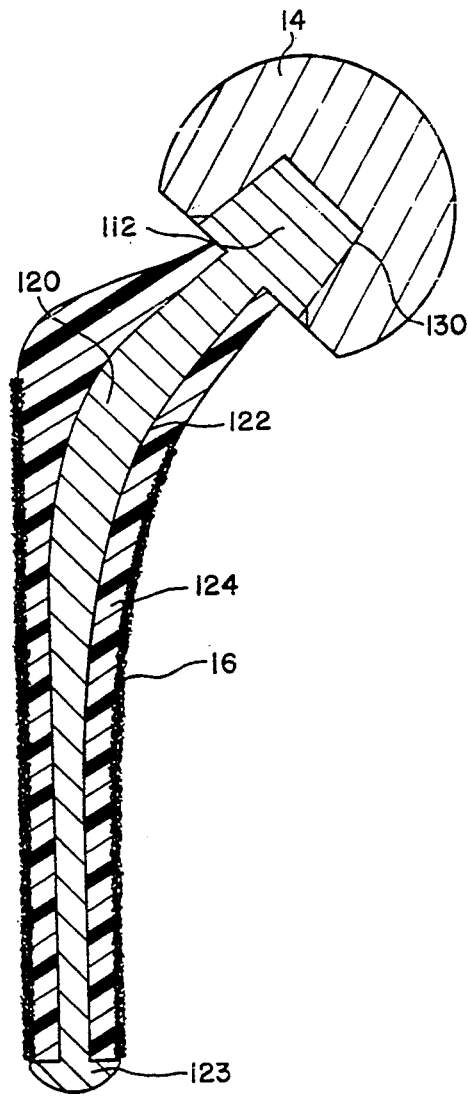
FIG. 2 is a view similar to FIG. 1 illustrating a second embodiment a hip prosthesis.

In the alternative embodiment of FIG. 2 the core 120 is substantially uniform in diameter with a slight increase in diameter at the proximal region 122 of the hip prosthesis 110. The polymer casing 124 extends from an end cap 123 to a neck 112 so that no collar is provided. The porous surface layer 16 is also embedded into the polymer casing and adhesively secured thereto.

Figure 3:
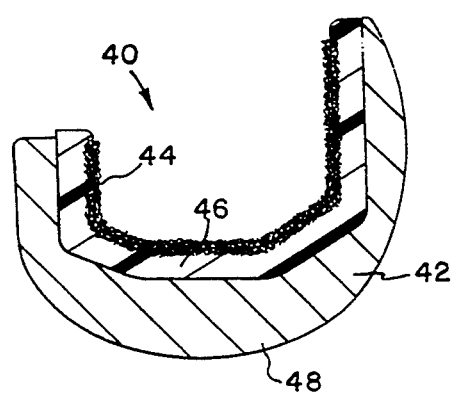
FIG. 3 is a side view of a femoral knee prosthesis that is cut away from front to back to illustrate the construction of the femoral knee prosthesis.
Figure 4:
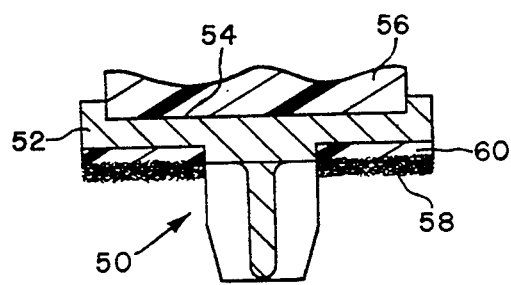
FIG. 4 is a front view of tibial knee prosthesis that is cut away transversely from side to side to illustrate the construction of the tibial knee prosthesis.

In FIG. 3 a femoral component 40 of a knee prosthesis is illustrated with a body 42 secured to a porous layer 44 by means of a thin layer of polymer 46 comprising Ultrapek KR 4177. The body 42 includes a contoured outer surface 48 to articulate relative to a bearing component, see FIG. 4. The porous layer 44 is adapted to intimately contact resected bone for bony ingrowth, or in the alternative to receive bone cement for fixation of the femoral component 40 to the distal end of a femur. A tibial component 50 of a knee prosthesis includes a tray 52 with a top recess 54 to receive the bearing component 56. A porous layer 58 is secured to the bottom of the tray by means of a thin layer of polymer 60 also comprising Ultrapek KR 4177. The polymer 60 partially penetrates into the porous layer in a heated process and intimately contracts the tray so that upon cooling the polymer is adhesively coupled to the tray and porous layer while also physically coupled to the latter by means of the partial penetration.

We claim:

1. An orthopaedic implant device comprising a body, a casing attached to the body and a porous metal surface layer attached to the casing and adapted for contact with the bone to receive bony ingrowth into the pores, the casing including adhesive characteristics for attachment to the body and porous metal surface layer, the improvement wherein, the body is a metal made from cobalt chrome and the porous metal surface layer is made from titanium.

2. An orthopaedic implant device comprising a body, a casing attached to the body and a porous metal surface layer attached to the casing and adapted for contact with the bone to receive bony ingrowth into the pores, the casing including adhesive characteristics for attachment to the body and porous metal surface layer, the improvement wherein, the casing is a thermoplastic polymer and the body and porous layer are made from different metals.

3. An orthopedic implant device comprising a metal body extending from a proximal end to a distal end, a polymer casing secured to the body and a porous metal surface layer secured to the polymer casing, the metal body extending outwardly from the polymer casing at the proximal end to form a neck of a hip prosthesis for engagement with a substantially spherical head which is adapted for articulation relative to an acetabulum of a patient receiving the hip prosthesis and the porous metal surface layer extends substantially from the neck to the distal end to provide the porous metal surface layer over substantially all of the polymer casing wherein, the metal body extends outwardly from the polymer casing at the distal end to form a metal cap substantially contiguous with the porous metal layer near the distal end.

4. The orthopaedic implant device of claim 3 in which the metal body further defines a collar extending transversely from the neck and substantially forming a proximal boundary for the polymer casing.

5. The orthopaedic implant device of claim 3 in which the metal body is made from cobalt chrome and the porous metal surface layer is made from titanium.

6. The orthopaedic implant device of claim 3 in which the polymer casing is polyaryletherketone which includes adhesive characteristics in a heated state to adhere to the metal body and the porous metal surface layer.

7. The orthopaedic implant device of claim 3 in which the porous metal surface layer is formed from titanium which is provided with a nitrided surface.

8. An orthopaedic implant device comprising a metal body extending from a proximal end to a distal end, a polymer casing secured to the body and a porous metal surface layer secured to the polymer casing, the metal body extending outwardly from the polymer casing at the proximal end to form a neck of a hip prosthesis for engagement with a substantially spherical head which is adapted for articulation relative to an acetabulum of a patient receiving the hip prosthesis and the porous metal surface layer extends substantially from the neck to the distal end to provide the porous metal surface layer over substantially all of the polymer casing wherein the metal body defines a diameter dimension that is reduced in a distal direction from the neck and the diameter dimension is enlarged at the distal end to form an end cap.

* * * * *